(12) United States Patent
Borsotti et al.

(10) Patent No.: US 10,208,271 B2
(45) Date of Patent: Feb. 19, 2019

(54) PROCESS FOR THE SELECTIVE HYDROGENATION OF VEGETABLE OILS

(71) Applicant: Novamont S.p.A., Novara (IT)

(72) Inventors: Giampietro Borsotti, Novara (IT); Luigi Capuzzi, Novara (IT); Francesca DiGioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 15/538,352

(22) PCT Filed: Dec. 21, 2015

(86) PCT No.: PCT/EP2015/080865
§ 371 (c)(1),
(2) Date: Jun. 21, 2017

(87) PCT Pub. No.: WO2016/102509
PCT Pub. Date: Jun. 30, 2016

(65) Prior Publication Data
US 2017/0362537 A1 Dec. 21, 2017

(30) Foreign Application Priority Data

Dec. 22, 2014 (IT) .............................. MI2014A2204

(51) Int. Cl.
*C11C 3/12* (2006.01)
*C07C 67/303* (2006.01)
*C07C 69/587* (2006.01)

(52) U.S. Cl.
CPC ............ *C11C 3/126* (2013.01); *C07C 67/303* (2013.01); *C07C 69/587* (2013.01); *C11C 3/123* (2013.01); *C07B 2200/09* (2013.01)

(58) Field of Classification Search
CPC . C11C 3/12; C11C 3/126; C11C 3/123; C07C 67/303; C07C 69/587
See application file for complete search history.

(56) References Cited

U.S. PATENT DOCUMENTS

| 3,865,853 | A | * | 2/1975 | Hinze | ...................... B01J 23/44 |
| | | | | | 554/145 |
| 4,326,932 | A | | 4/1982 | Fröling et al. | |
| 8,222,438 | B2 | * | 7/2012 | Bastioli | ................. C07C 51/245 |
| | | | | | 554/123 |

FOREIGN PATENT DOCUMENTS

| EP | 0 021 527 A1 | 1/1981 | | |
| EP | 0 021 528 A1 | 1/1981 | | |
| FR | 2 503 180 A1 | 10/1982 | | |
| FR | 2503180 | * 10/1982 | ............... | C11C 3/12 |
| WO | WO-2005/095306 A1 | 10/2005 | | |
| WO | WO 2011/080296 | * 7/2011 | ........... | C07C 51/245 |

OTHER PUBLICATIONS

FR 2503180, Cecchi Georges, et al, Selective hydrogenation of polyunsaturated fatty acid—in vegetable oil, over palladium at low temp. 1982, 21 pages, English translation (Year: 1982).*

* cited by examiner

*Primary Examiner* — Yate' K Cutliff
(74) *Attorney, Agent, or Firm* — Polsinelli PC

(57) ABSTRACT

Process for the catalytic hydrogenation of vegetable oils wherein the oil is placed in contact with molecular hydrogen in the presence of a metal catalyst, and the process is performed in the absence of water or in the presence of a quantity of water equal to or less than 5:1 with respect to the weight of the metal catalyst and at a temperature equal to or less than 50° C.

21 Claims, No Drawings

PROCESS FOR THE SELECTIVE HYDROGENATION OF VEGETABLE OILS

CROSS REFERENCE TO RELATED APPLICATIONS

This application is a National Phase filing under 35 U.S.C. § 371 of PCT/EP2015/080865 filed on Dec. 21, 2015; and this application claims priority to Application No. MI2014A002204 filed in France on Dec. 22, 2014 under 35 U.S.C. § 119. The entire contents of each application are hereby incorporated by reference.

The present invention relates to a process for the selective hydrogenation of vegetable oils. In particular this invention relates to a process for the hydrogenation of vegetable oils which is capable of selectively converting polyunsaturated fatty acids into mono-unsaturated fatty acids and the products obtained therefrom. The vegetable oils obtained by the process according to the invention have in particular a high mono-unsaturated fatty acids content and are particularly suitable for use as raw materials for the synthesis of chemical intermediates.

Vegetable oils are now an important raw material for the chemical industry on account of the increasingly pressing need to identify raw materials of renewable origin which are alternatives to conventional oil-based sources.

For example WO2008/138892 describes a process of oxidative cleavage which, starting from vegetable oils containing mono-unsaturated fatty acid triglycerides, makes it possible to produce intermediates which are important for the preparation of polyesters, such as for example the saturated dicarboxylic acids azelaic acid or brassylic acid.

As is known, vegetable oils comprise mixtures of fatty acid triglycerides. These fatty acids generally contain from 16 to 22 carbon atoms and may be saturated, for example stearic acid, mono-unsaturated, for example oleic acid, or polyunsaturated, such as for example linoleic acid and linolenic acid.

These vegetable oils have quite different compositions, depending upon the nature of the plant species from which they are obtained, for example different types and contents of mono-unsaturated fatty acids. This constitutes an appreciable limitation on the use of vegetable oils as raw materials for the organic chemical industry.

It has therefore become necessary to find and make use of processes to modify the composition of vegetable oils in order to encourage their use in this sector.

For example, hydrogenation processes have wide application in the chemical field, and in particular in the field of oil chemistry. The double bonds present in the chains of unsaturated fatty acids can in fact be saturated by the addition of hydrogen in the presence of catalysts such as for example nickel, platinum, palladium or copper. The hydrogenation processes are exothermic and the reaction rate depends on the type of oil, the temperature, the activity and concentration of the catalyst, and the hydrogen pressure. Although widely used, these processes nevertheless have appreciable limitations from the point of view of selectivity. In particular the possibility of maintaining high conversions of polyunsaturated fatty acids while avoiding the formation of saturated fatty acids is limited.

A system for increasing the selectivity is that of increasing the reaction temperature. However this may result in the occurrence of isomerization reactions of the unsaturated fatty acids present in the vegetable oil. As is known, the unsaturated fatty acids present in vegetable oils in nature are mainly of the cis type. Under high temperature conditions these cis acids can engage in isomerisation reactions and become converted into trans isomers. In general the trans isomers have higher melting points than the cis isomers and beyond particular levels of conversion this can give rise to the formation of a solid phase which for example contains trans 9-octadecenoic acid.

When compared to naturally occurring vegetable oils, the vegetable oil containing trans isomers are also less susceptible to oxidation reactions by peroxides. This determines longer reaction times when said oils are subjected to oxidative cleavage reactions.

There therefore exists the need to develop new processes for selective hydrogenation of vegetable oils, able to convert selectively the polyunsaturated fatty acids into monounsaturated fatty acids, while limiting the isomerization reactions which result in the formation of trans isomers.

Considering this problem it has now been surprisingly discovered that, by operating at low temperatures in the presence of a metal catalyst and limited amounts of water or without water, it is possible to obtain a significant conversion of the polyunsaturated fatty acids of the triglycerides present in the oil while increasing or at least maintaining the selectivity with respect to monounsaturated fatty acids of the cis type. These advantageous effects are obtained even using small amounts of catalyst and at atmospheric pressure or a pressure slightly higher than atmospheric pressure.

In particular, the present invention relates to a process for the catalytic hydrogenation of vegetable oils in which the oil is placed in contact with molecular hydrogen in the presence of a metal catalyst, characterized in that said process is conducted in the absence of water or in any case in the presence of a quantity of water equal to or less than 5:1, preferably less than 5:1, more preferably equal to or less than 4:1, even more preferably equal to less than 1.5:1 relative to the weight of the metal catalyst, and at a temperature less than or equal to 50° C., preferably less than 25° C., more preferably less than 20° C. and even more preferably less than or equal to 18° C.

It has in fact been surprisingly discovered that, by operating in these conditions, it is possible to improve the catalytic activity and selectivity of the metal catalysts as regards the hydrogenation of the polyunsaturated fatty acids of the triglycerides present in the oil. Particularly suitable for this purpose are the catalysts containing metallic palladium, preferably on a carbon or alumina support.

As a result of the process according to the present invention, it is in fact possible to selectively convert the polyunsaturated fatty acids into monounsaturated fatty acids and also limit the isomerization reactions with formation of trans isomers and obtain an oil with a high content of monounsaturated fatty acids, particularly suitable for then being used as raw material for the synthesis of chemical intermediates.

As a result of this composition, the vegetable oil obtained from the process according to the invention is particularly suitable for being used as a starting material, also mixed with other vegetable oils, for oxidative scission processes in which inorganic and organic peroxides, peracids, nitric acid, permanganates, periodates, $O_2$, $O_3$ or gaseous mixtures thereof are used as oxidizing agents.

Oxidative scission processes which use peroxides, such as hydrogen peroxide, and $O_2$ or mixtures containing $O_2$ as oxidizing agents are preferred. Specific examples are the oxidative scission processes described in the applications WO 2008/138892, WO 2011/080296 or WO 2013/079849 A1.

The vegetable oil obtained from the process according to the present invention is even more useful as a starting material for oxidative scission processes comprising the steps of:
a) reacting the triglycerides of unsaturated carboxylic acids with an oxidizing compound, preferably in the presence of a catalyst able to catalyze the oxidation reaction of the olefinic double bond, obtaining an intermediate compound containing vicinal diols;
b) reacting said intermediate compound with oxygen, or a gaseous mixture containing oxygen, preferably in the presence of a catalyst able to catalyze the oxidation reaction of the vicinal diols to carboxyl groups, obtaining saturated monocarboxylic acids and triglycerides containing saturated dicarboxylic acids.

When the vegetable oil obtained from the process according to the present invention is used as a raw material for oxidative scission processes in mixtures with other vegetable oils, preferably said mixtures contain more than 10% of the vegetable oil obtained from the process of the present invention.

When present, the quantity of water during the reaction may vary, remaining in any case equal to or preferably less than 5:1, more preferably equal to or less than 4:1, even more preferably equal to or less than 1.5:1 relative to the weight of the metal catalyst. The water may be present from the start of the reaction or introduced gradually during the course of the reaction, for example by means of saturation of specific amounts of hydrogen gas.

Advantageously, water in addition to that present in the catalyst is not added.

According to a preferred aspect of the present invention the water is absent during the course of the reaction.

By using the process according to this invention it is possible to hydrogenate vegetable oils such as: soya oil, olive oil, castor oil, sunflower oil, safflower oil, peanut oil, maize oil, palm oil, jatropha oil, cardoon oil such as from *Cynara cardunculus, Silybum marianum*, cuphea oil, Brassicaceae oils such as from *Crambe abyssinica, Brassica carinata, Brassica napus* (rape), *Lesquerella*, or mixtures thereof. Waste frying oils or other exhausted vegetable oils can also be hydrogenated according to this invention. The use of sunflower oil, Brassicaceae oils, or cardoon oils such as those from *Cynara cardunculus* and *Sylibum marianum* is particularly preferred.

In particular the latter are obtained from plant species belonging to the Cardoon family, which are very robust annual or perennial herbaceous plants having the further advantage that they can be cultivated in arid areas with poorly favourable climates.

The process catalyst according to the present invention comprises a metal catalyst, preferably on a support, and may be used in the form of a sheet, particle or sphere with dimensions typically of between 2 and 4 mm.

Examples of metal catalysts which may be used are nickel, platinum, palladium, osmium, iridium, copper, iron, rhodium, ruthenium, molybdenum, tungsten and mixtures thereof.

According to a preferred aspect of the invention, the metal catalyst used comprises palladium, in amounts generally of between 20 mg/kg and 500 mg/kg, preferably between 30 and 100 mg/kg, more preferably between 40 and 50 mg/kg relative to the amount of vegetable oil to be hydrogenated. The amount of catalyst may vary, within this range, depending on the form of the catalyst, the surface area thereof and the concentration of the metal catalyst with respect to any support. Typically, the catalyst comprises 0.1-5% by weight of metallic palladium; preferably the catalyst comprises 0.1-1% and more preferably 0.1-0.5% by weight of metallic palladium.

Preferably, the catalyst comprises metal in a form supported on any support known in the art, for example on alumina, carbon in different forms and also in the form of nanotubes, $CeO_2$, $ZrO_2$, $CrO_2$, $TiO_2$, MgO, silica, inorganic/organic sol-gel matrices, polycrystalline oxide substrates, amorphous carbon, zeolites, aluminosilicates, alkaline-earth carbonates such as magnesium carbonate, calcium carbonate or barium carbonate, barium sulphate, montmorillonites, polymer matrices, polyfunctional resins, ion-exchange resins, ceramic supports or a mixture of two or more thereof. In a preferred embodiment of the process, the catalyst comprises metallic palladium on an alumina or carbon support. Even more preferably the catalyst comprises metallic palladium on an alumina support.

The supported catalyst may be prepared using techniques known to the person skilled in the art, for example by finely dispersing a metal salt on the support and then reducing the salt of the metal to the metallic state. The metal salt dispersion step may for example be performed by means of impregnation, absorption by a solution, co-precipitation or deposition, for example by means of chemical vapour deposition. The metal salt reduction step is typically performed by heating the metal salt supported in the presence of a molecular hydrogenation atmosphere. The catalyst preparation step may be conducted separately from the hydrogen process according to the present invention or may take place during a preliminary phase thereof. For example, the metal salt supported may be introduced into the hydrogenation reactor and reduced in situ in a hydrogen atmosphere before the addition of the vegetable oil. Particularly suitable catalysts for use in the process according to the present invention are, for example, palladium supported on γ-alumina with 0.2% by weight of palladium ("G68G" produced by Sud Chemie), palladium supported on γ-alumina with 0.3% by weight of palladium (produced by Johnson Matthey) and palladium supported on γ-alumina with 0.5% by weight of palladium in the form of 2.4-4 mm spheres ("AMS-5" produced by Engelhard). Advantageously, the catalyst is recovered at the end of the reaction and recycled in successive hydrogenation reactions.

Among the advantages of the process according to the present invention there is the fact that it may be conduced in particular in the presence of palladium-based catalysts, without the need to add to the catalyst promoters for improving the selectivity, such as copper, silver, zinc, tin, lead, titanium, zirconium, hafnium, vanadium, niobium, tantalum, chromium, molybdenum, tungsten or manganese.

In general, the process according to the present invention may be conducted in one or more special apparatus such as stirred reactors, fixed-bed reactors, moving-bed reactors, driven-bed and fluidized-bed reactors or airlift reactors. At the end of the reaction, the catalyst may be easily recovered by means of known techniques and reused several times. In a preferred embodiment, the process for catalytic hydrogenation of vegetable oils according to the present invention comprises a step during which the catalyst is separated from the vegetable oil, for example by means of filtration or decantation.

In the case of stirred reactors, in particular, stirring of the means helps determine the speed of diffusion of the hydrogen and the degree of contact between the vegetable oil and hydrogen. Depending on the volume and the configuration of the reactor, stirring speeds ranging for example between 100 and 1200 rpm, more particularly between 200 and 1000 rpm, may be used. The stirring speed of the system is preferably between 500 and 1000 rpm.

The hydrogenation reaction is conducted at temperatures less than or equal to 50° C., preferably between 30 and 0° C., more preferably between 25 and 0° C. and even more preferably between 20 and 0° C., for example between 3 and 18° C. The temperature may be regulated for example by heating the reaction mixture before the start of the reaction. Since the hydrogenation reaction is exothermic, as it progresses there is a gradual increase in the temperature inside the reaction mixture. Said increase is typically regulated by means of cooling systems which prevent overheating thereof, which could alter the progress of the reaction.

As regards the molecular hydrogen, the hydrogenation reaction according to the present invention is typically conducted at molecular hydrogen pressures of between 1 and 15 bar, preferably between 1 and 10 bar, more preferably between 1 and 5 bar, while keeping the total pressure below 20 bar, preferably below 15 bar and more preferably below 10 bar. Depending on the requirements, it is possible to introduce the hydrogen into the reactor continuously, adjusting the flow thereof, or supplying it by means of one or more aliquots, for example 3, 5 or 7 aliquots, while keeping the hydrogen pressure within the abovementioned range.

The process is advantageously carried out in the presence of organic solvents, preferably selected from among hydrocarbons, esters, ketones, C3-C6 alcohols, ethers such THF, in order to decrease the viscosity of the system and increase the reaction speed. Preferred organic solvents are those which may be easily recovered, for example by means of distillation. Specific examples of suitable organic solvents are petroleum ether, hexane, heptane, octane, ethyl acetate and toluene.

The weight ratio between organic solvent and oil is preferably between 0.25:1 and 3:1, and more preferably between 0.5:1 and 2:1.

Additives such as bases can be added in order to further improve the selectivity of the hydrogenation reaction as known in the art. Examples of said bases are amines, oxides, hydroxydes, or carbonates of alkali metals, alkaline earth metals or ammonium. Specific examples of bases are N-ethyldiisopropylamine, triethylamine, diamines such as ethylenediamine, its homologues and/or derivatives such as tetramethylethylenediamine, tetraalkyl amines, where the alkyl chain are for example C2 to C6 alkyl chains, cyclic amines such as diazabicyclooctane or diazabicycloundecene, ammonium hydroxide salts such as choline or tetrabutylammonium hydroxide. Choline or tetrabutylammonium hydroxide are advantageously used in the presence of a co-solvent such as methanol when petroleum ether is used as solvent for the vegetable oil. In this case the methanol solubilizes the tetrabutylammonium hydroxide and forms a separated phase in which the catalyst will partition at the end of the reaction, facilitating the recovery.

The process can be controlled in a manner known to those skilled in the art, for example by measuring the pressure within the reactor and interrupting the reaction when a specific quantity of hydrogen has been absorbed.

As an alternative the course of the reaction can be monitored by sampling and analysing the composition of the reaction mixture. The theoretical amount of hydrogen required for the completion of the reaction can be easily determined on the basis of the composition of the starting vegetable oil for example by analyzing the amount of unsaturations.

The duration of the process according to this invention depends on the nature of the vegetable oil, the operating conditions, the desired conversion, and the dimensions of the reactor used, and is typically from 5 minutes to 6 hours, for example from 60 to 300 minutes.

According to a preferred aspect, the hydrogenation reaction according to the present invention is carried out at temperatures of between 0 and 30° C., more preferably between 0 and 25° C. and even more preferably between 0 and 18° C., and preferably keeping the molecular hydrogen pressure between 1 and 2 bar, and more preferably between 1 and 1.5 bar. By adopting the said reaction conditions, a conversion of triglycerides of polyunsaturated acids higher than 50%, more advantageously higher than 70% and even higher than 75%, is advantageously achieved with the present process, while keeping the selectivity towards triglycerides of monounsaturated acids high, preferably higher than 80% and more preferably higher than 90%.

Interestingly, the trans-isomerization degree of the monounsaturated acids formed by hydrogenation of polyunsaturated acids according to the present process is remarkably low, the trans isomers being typically less than 50%, advantageously less than 40% and more advantageously less than 30% of the formed monounsaturated acids, and typically less than 15% of the total fatty acid content.

According to a particularly preferred aspect, the reaction is carried out at temperatures of below 18° C., preferably of between 15 and 3° C., and at a $H_2$ pressure of below 5 bar, preferably of 1-2 bar. By operating in such conditions it is in fact possible to achieve a conversion of triglycerides of polyunsaturated acids to triglycerides of monounsaturated acids particularly high, at the same time obtaining a high selectivity with respect to triglycerides of monounsaturated acids of the cis type, even without the need for additives such as amines. The trans-isomerization degree of the monounsaturated acids formed by hydrogenation is in fact significantly lower than that obtained at temperatures above 18° C.

By carrying out the process at temperatures of less than 20° C. an organic solvent is advantageously used, due to the increase in the oil viscosity. Notwithstanding the present process requires a limited amount of solvent to achieve a satisfactory conversion; for example amounts of solvent from 1.0:1 to 2.0:1 by weight with respect to the oil are advantageously used, more advantageously from 1.0:1 to 1.5:1, at temperatures of less than or equal to 18° C.

A further advantage of the present invention consists of the composition of the resultant hydrogenated oil, which has a content of diunsaturated acids and monounsaturated acids and a content of cis isomers which make it particularly suitable for undergoing oxidative scission processes. Processes which use peroxides, such as hydrogen peroxide, and $O_2$ or mixtures containing $O_2$ as oxidizing agents are preferred. In particular, said oils are particularly suitable for being used as starting material for the oxidative scission processes described in WO 2008/138892, WO 2011/080296 or WO 2013/079849. Preferably said hydrogenated oil is characterized by:
  a content of diunsaturated acids of less than 10% by weight, preferably less than 5%, relative to the total content of fatty acids;
  a content of mono-unsaturated acids of more than 70% by weight relative to the total content of fatty acids, preferably greater than 75%, of which the 9-cis isomers and 12-cis isomers constitute preferably more than 80%, and more preferably more than 85%.

a content of mono-unsaturated trans isomers higher than 1.5% and less than 15%, preferably greater than 2% and less than 10% by weight relative to the total content of fatty acids.

The present invention also refers to a vegetable oil characterized by:
- a di-unsaturated acids content of less than 10% by weight, preferably less than 5%, with respect to the total fatty acids content;
- a mono-unsaturated acid content of more than 70% by weight with respect to the total fatty acids content, preferably of more than 75%, of which, of which 9-cis and 12-cis isomers are preferably more than 80%, more preferably more than 85%;
- a trans mono-unsaturated isomer content higher than 1.5% and lower than 15%, preferably higher than 2% and lower than 10% by weight with respect to the total fatty acids content, which is particularly suitable for being used as starting material for oxidative scission processes for producing intermediates useful for the preparation of polyesters.

In particular, with a content of the oil of monounsaturated trans acids ranging from 1.5% to 15% it is possible to carry out oxidative scission processes which use hydrogen peroxide and/or $O_2$ as oxidizing agents without influencing the reaction times.

Said oil may be advantageously obtained by subjecting a vegetable oil, preferably a cardoon oil, to the hydrogenation reaction according to the present invention at temperatures preferably between 0 and 25° C. and more preferably between 3 and 15° C., in the presence of an organic solvent.

Said oil is preferably used as starting material for oxidative cleavage processes comprising the steps of:
a) causing the unsaturated carboxylic acid triglycerides to react with an oxidising compound, preferably in the presence of a catalyst capable of catalysing the reaction of oxidising the olefin double bond to obtain an intermediate compound containing vicinal diols;
b) causing the said intermediate compound to react with oxygen, or a gaseous mixture containing oxygen, preferably in the presence of a catalyst capable of catalysing the reaction of oxidising the vicinal diols to carboxyl groups obtaining saturated monocarboxylic acids and triglycerides containing saturated dicarboxylic acids.

The invention will now be illustrated with a number of examples which are intended to be merely illustrative and do not limit the invention.

EXAMPLES

In the following examples the carboxylic acid composition of the oil was determined after transesterification of an oil sample (140 μl) in 140 μl of methanolic KOH (2N). The methyl esters of the carboxylic acids were extracted from the methanolic solutions in 3 ml of hexane and then analyzed in a gas chromatograph equipped with flame ionization detector (FID) and a capillary column SLB-IL111 100 m×0.25 mm×0.2 micron (SUPELCO) at a constant pressure of 275 kPa.

Temperature programme of the oven: 100° C. (35 min)—2.5° C./min—140° C. (30 min)—5.0° C./min—260° C. (25 min) for a total time of 130 min.

Temperature of the injector: 250° C.; split ratio=250:1; carrier gas:helium.

The conversion of diunsaturated acids (C18: 2) was determined as follows:

$$\frac{(\Sigma \text{ starting } C18:2 - \Sigma \text{ final } C18:2)}{\Sigma \text{ starting } C18:2},$$

where $\Sigma$ starting C18: and $\Sigma$ final C18:2 correspond to the sum of the % weight of the various isomers of the diunsaturated C18 acids relative to the total carboxylic acid composition, before and after the hydrogenation reaction, respectively.

The selectivity with respect to the monounsaturated acids (C18:1) was determined as follows:

$$\frac{(\Sigma \text{ final } C18:1 - \Sigma \text{ starting } C18:1)}{(\Sigma \text{ starting } C18:2 - \Sigma \text{ final } C18:2)}$$

where final $\Sigma$ C18:1 and $\Sigma$ starting C18:1 correspond to the sum of the % weight of the various isomers of monounsaturated C18 acids relative to the total carboxylic acid composition, after and before the hydrogenation reaction, respectively, and $\Sigma$ starting C18:2 and $\Sigma$ final C18:2 correspond to the sum of the % weight of the various isomers of the diunsaturated C18 acids relative to the total carboxylic acid composition, before and after the hydrogenation reaction, respectively.

The trans-isomerization degree of the monounsaturated acids formed by hydrogenation was determined as follows:

$$\frac{\Sigma C18:1 \text{ trans}}{(\Sigma \text{ final } C18:1 - \Sigma \text{ starting } C18:1)}$$

where $\Sigma$ C18:1 trans corresponds to the sum of the % by weight of the trans isomers of monounsaturated C18 acids relative to the total carboxylic acid composition after the hydrogenation reaction, and $\Sigma$ final C18:1 and $\Sigma$ starting C18:1 correspond to the sum of the % weight of the various isomers of monounsaturated C18 acids relative to the total carboxylic acid composition, after and before the hydrogenation reaction, respectively.

Example 1 (Comparative)

500 g of sunflower oil containing 56% by weight of linoleic acid with respect to the total fatty acids content were hydrogenated in an autoclave fitted with a stirrer in the presence of 15.5 g of catalyst based on palladium supported on γ-alumina (0.2% by weight of Pd—"G68G" produced by Sud Chemie) at a temperature of 118° C., maintaining a hydrogen pressure between 2 and 5 bar. The reaction was interrupted after 80 minutes. The conversion of linoleic acid, determined by gas chromatographic analysis, was 34.5%, with selectivity for mono-unsaturated acids of 28.9%.

Example 2

The hydrogenation reaction was carried out in a cylindrical reactor with 500 ml capacity, equipped with electromagnetic stirrer and thermometer and connected to a hydrogen cylinder by means of mass flow meter.

The reactor was charged with 50 g of cardoon oil, 150 ml (96 g) of petroleum ether and 0.84 g of catalyst in powder form consisting of 0.3% Pd/$Al_2O_3$ (Johnson Matthey; initial water content of 4.2% by weight), previously dried in vacuo at 80° C. for 2 hours (final water content of 1.13% corresponding to a weight ratio H2O:Pd of 3.8:1).

The reactor was connected to a pump in order to remove the air and then fed with a stream of H₂ with a flowrate of 30 ml/minute.

The reactor was stirred vigorously for 110 minutes at 700 rpm, while maintaining a temperature of 5-6° C. in a cryostat. By means of a reactor output counter the quantity of absorbed hydrogen was measured, the value being equal to 2.71.

The catalyst was filtered and the organic solvent was evaporated in order to obtain the hydrogenated cardoon oil. The percentage weight composition of C18 carboxylic acids of the hydrogenated oil relative to the total carboxylic acid composition as measured by means of GC analysis after 110 minutes' reaction, relative to the composition of the cardoon starting oil, is shown in Table 1.

The conversion of linoleic acid was equal to 85% and the selectivity with respect to the oleic acid was 90%. As can be easily calculated from the data in Table 1, the trans-isomerization degree of the monounsaturated C18 acids formed by hydrogenation is of merely 18.6%.

TABLE 1

| Carboxylic acid composition | Cardoon oil | Example 2 | Example 3 |
|---|---|---|---|
| Hydrogenation time | — | 110 mns | 137 mns |
| Hydrogenation Temperature | — | 5-6° C. | 20° C. |
| C 18:0 | 3.2 | 7.4 | 7.8 |
| C 18:1 cis | 25.6 | 63.3 | 64.5 |
| C 18:1 trans | — | 8.6 | 13.5 |
| C 18:2 | 59.4 | 8.9 | 2.55 |
| C 18:3 | 0.2 | — | — |
| Conversion C18:2 | — | 85% | 95.7% |
| Selectivity C18:1 | — | 91.7% | 92.3% |
| 9-cis C18:1/Σ C18:1 | 96.7% | 62.0% | 59.0% |
| 12-cis C18:1/Σ C18:1 | — | 24.7% | 22.7% |
| trans-isomerization degree of C18:1 formed | — | 18.6% | 25.7% |

Example 3

The hydrogenation reaction was carried out in the same reactor as that used in Example 2 with 50 g of cardoon oil, 50 g of petroleum ether and 0.757 g of catalyst in powder form consisting of 0.33%/Al₂O₃ (Johnson Matthey; water content equal to 0.4% by weight), with a resultant H₂O:Pd weight ratio of 1.2:1.

The reactor was connected to a pump in order to remove the air and then fed with a stream of H₂ with a flowrate of 30 ml/minute.

The reactor was stirred vigorously for about 137 minutes at 700 rpm, while maintaining a temperature of 20° C. in a cryostat. By means of a reactor output counter the quantity of absorbed hydrogen was measured, the value being equal to 2.71.

The catalyst was filtered and the organic solvent was evaporated in order to obtain the hydrogenated cardoon oil. The percentage composition by weight of C18 carboxylic acids of the hydrogenated oil is shown in Table 1.

The conversion of linoleic acid in presence of a water/Pd ratio of 1.2:1 was more than 95% and the selectivity with respect to the oleic acid higher than 90%, maintaining a selectivity with respect to the cis isomers higher than 80%. As can be seen from Table 1, the trans-isomerization degree after the hydrogenation reaction performed at 20° C. is of 25.7%.

The invention claimed is:

1. A process for the selective conversion of polyunsaturated fatty acids into monounsaturated fatty acids of triglycerides present in vegetable oils, with a trans-isomerization degree of less than 50% of the formed monounsaturated fatty acids, wherein the oil is placed in contact with molecular hydrogen in the presence of a metal catalyst, wherein said process is performed in the absence of water or in the presence of a quantity of water equal to or less than 5:1 with respect to the weight of the metal catalyst and at a temperature from 18 to 3° C. and for a duration of from 5 minutes to 6 hours.

2. The process according to claim 1, wherein said metal catalyst is selected from nickel, platinum, palladium, osmium, iridium, copper, iron, rhodium, ruthenium, molybdenum, tungsten and mixtures thereof.

3. The process according to claim 2, wherein said metal catalyst comprises metallic Palladium.

4. The process according to claim 3, wherein the conversion is performed in the presence of 20 mg/kg-500 mg/kg of metallic Palladium with respect to the vegetable oil.

5. The process according to claim 3, wherein said metal catalyst comprises 0.1-5% by weight of metallic Palladium.

6. The process according to claim 1, wherein said metal catalyst is supported.

7. The process according to claim 6, wherein the support of said metal catalyst is selected from alumina, carbon, CeO₂, ZrO₂, CrO₂, TiO₂, MgO, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulfate, montmorillonites, polymer matrices, ion-exchange resins, polyfunctional resins, ceramic supports or a mixture of two or more thereof.

8. The process according to claim 7, wherein the catalyst comprises metallic Palladium supported on alumina or carbon.

9. The process according to claim 1, wherein the said process is performed at a molecular Hydrogen pressure of from 1 to 15 bar.

10. The process according to claim 9 wherein the molecular Hydrogen pressure is of below 5 bar.

11. The process according to claim 1 performed in the presence of a organic solvent selected from hydrocarbons, esters, ketones, C3-C6 alcohols, and ethers.

12. The process according to claim 11, wherein the weight ratio of organic solvent to vegetable oil is from 0.25:1 to 3:1.

13. The process according to claim 12, wherein the weight ratio of organic solvent to vegetable oil is from 1:1 to 2:1.

14. A process for the selective conversion of polyunsaturated fatty acids into monounsaturated fatty acids of triglycerides present in vegetable oils selected from sunflower oil, oils from Brassicaceae or Cardoon oils, with a trans-isomerization degree of less than 50% of the formed monounsaturated fatty acids, the said conversion being performed using a metal catalyst and in the absence of water or in the presence of a quantity of water equal to or less than 5:1 with respect to the weight of the metal catalyst and at a temperature equal of 18 to 3° C. and for a duration of from 5 minutes to 6 hours.

15. The process according to claim 4, wherein said metal catalyst comprises 0.1-5% by weight of metallic Palladium.

16. The process according to claim 2, wherein the said process is performed at a molecular Hydrogen pressure of from 1 to 15 bar.

17. The process according to claim 3, wherein the said process is performed at a molecular Hydrogen pressure of from 1 to 15 bar.

18. The process according to claim 4, wherein the said process is performed at a molecular Hydrogen pressure of from 1 to 15 bar.

19. The process according to claim 5, wherein the said process is performed at a molecular Hydrogen pressure of from 1 to 15 bar.

20. The process according to claim 1, wherein the duration is from 60 minutes to 300 minutes.

21. The process according to claim 14, wherein the duration is from 60 minutes to 300 minutes.

\* \* \* \* \*